US007751878B1

(12) United States Patent
Merkle et al.

(10) Patent No.: US 7,751,878 B1
(45) Date of Patent: Jul. 6, 2010

(54) REAL-TIME HUMAN COLLABORATION MONITORING AND INTERVENTION

(75) Inventors: Peter B. Merkle, Sandia Park, NM (US); Curtis M. Johnson, Sandia Park, NM (US); Wendell B. Jones, Albuquerque, NM (US); Gerold Yonas, Albuquerque, NM (US); Adele B. Doser, Albuquerque, NM (US); David J. Warner, Rancho Santa Fe, CA (US)

(73) Assignee: Sandia Corporation, Albuquerque, NM (US)

( * ) Notice: Subject to any disclaimer, the term of this patent is extended or adjusted under 35 U.S.C. 154(b) by 1055 days.

(21) Appl. No.: 11/271,214

(22) Filed: Nov. 10, 2005

Related U.S. Application Data

(60) Provisional application No. 60/626,532, filed on Nov. 10, 2004.

(51) Int. Cl.
*A61B 5/04* (2006.01)
(52) U.S. Cl. ..................... 600/545; 600/544
(58) Field of Classification Search ................. 600/545
See application file for complete search history.

(56) References Cited

U.S. PATENT DOCUMENTS 5,046,504 A * 9/1991 Albert et al. ............... 600/509
5,584,291 A * 12/1996 Vapola et al. ............... 600/301
6,309,342 B1 * 10/2001 Blazey et al. ................ 600/26
6,450,820 B1 * 9/2002 Palsson et al. .............. 434/236
7,331,870 B2 * 2/2008 Smith et al. .................. 463/36
2007/0032732 A1 * 2/2007 Shelley et al. ............... 600/504

OTHER PUBLICATIONS

Doser, Adele B., et al., "Enabling Technology for Human Collaboration", *Sandia Report SAND 2003-4225*, Sandia National Laboratories,(Nov. 2003).
Scerbo, Mark W., et al., "The Efficacy of Psychophysiological Measures for Implementing Adaptive Technology", *NASA/TP-2001-211018*, National Aeronautics and Space Administration, Hampton, VA,(Jun. 2001).

* cited by examiner

*Primary Examiner*—Patricia C Mallari
(74) *Attorney, Agent, or Firm*—Robert D. Watson

(57) ABSTRACT

A method of and apparatus for monitoring and intervening in, in real time, a collaboration between a plurality of subjects comprising measuring indicia of physiological and cognitive states of each of the plurality of subjects, communicating the indicia to a monitoring computer system, with the monitoring computer system, comparing the indicia with one or more models of previous collaborative performance of one or more of the plurality of subjects, and with the monitoring computer system, employing the results of the comparison to communicate commands or suggestions to one or more of the plurality of subjects.

20 Claims, 7 Drawing Sheets
(6 of 7 Drawing Sheet(s) Filed in Color)

REAL-TIME HUMAN COLLABORATION MONITORING AND INTERVENTION

CROSS-REFERENCE TO RELATED APPLICATIONS

This application claims priority to and the benefit of the filing of U.S. Provisional Patent Application Ser. No. 60/626,532, filed on Nov. 10, 2004, and the specification and claims thereof are incorporated herein by reference.

STATEMENT REGARDING FEDERALLY SPONSORED RESEARCH OR DEVELOPMENT

The Government has rights to this invention pursuant to Contract No. DE-AC04-94AL85000 awarded by the U.S. Department of Energy.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to methods and apparatuses for human collaboration monitoring and intervention.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Many small group tasks are vital to security operations. For example, tactical operation centers and counter-terrorism intelligence analysis teams operate in fast-paced, data-rich, information-poor settings where task performance error can have catastrophic consequences. Emergency operations centers like any future national Infrastructure Operations Center can face similar challenges of time, data overload, interpersonal obstacles, and mission criticality.

By 2010, a convergence of information and communications technology is foreseen that will allow design and operation of a completely novel human-machine system. This system will enable and support those human functions best performed by humans, while more fully exploiting machine capabilities. In a possible future, people will have dedicated appliances or "PALs", which continuously integrate information about the human into an adaptive group system architecture referred to as "MENTOR". Physiologic, personality, attention, and interpersonal factors are among the kinds of data that can serve as bases for algorithms enabling higher group performance. Humans and computers are thus not separate systems, but a single complex adaptive system with both autonomous explicit self-models and goals in the context of the human group's mission.

Any group of people with reasonable freedom to act comprises a complex adaptive system. Traditional approaches to information system design do not leverage the qualities of complex adaptive systems nor do they plan for the adaptability and evolution of such systems. Designs are more or less static and assume that the system can be constrained to certain tasks, means, and structures, without unintended consequences. These approaches fail to leverage human strengths and are not robust in rapidly changing environments or for unanticipated circumstances.

The introduction to a human group of technologies (even simple ones) with broad utility is known often to result in emergent properties and dramatic changes in performance and how work is done. Use of commercial office software, cell phones, pagers, e-mail, chatrooms, on-line games, on-line shopping, product barcoding, videoconferencing, and group collaboration software are all examples of technologies that have changed the way people think and work. In each case, many of these changes were unanticipated and resulted in new behavior and results.

The use of physiologic data and other monitoring (audio, video) creates opportunities for machine customization and adaptation to the individual based on attributes such as attentiveness, current focus of attention, emotional state, stress level, learning and social styles, and current level of knowledge or expertise. The analysis of this data can also be fed back to individuals or groups to improve knowledge management, and increase self- and group awareness. This awareness can increase learning and adaptation.

The full realization of this vision is dependent upon continuing growth of technologies in diverse fields, including high-bandwidth wireless personal communications, unobtrusive and non-invasive physiologic sensors, neuroscience, several social sciences, and real-time integration of small group dynamic models with cybernetic monitoring and assessment.

However, the present invention provides effective methods and systems for monitoring human collaborative activities and the ability to provide real-time intervention into such activities. Details of the invention and its testing may be found in A. Doser, et al., "Enabling Technology for Human Collaboration", Sandia National Laboratories Report No. SAND 2003-4225 (Nov. 10, 2003).

BRIEF SUMMARY OF THE INVENTION

The present invention is of a method of and apparatus for monitoring and intervening in, in real time, a collaboration between a plurality of subjects, comprising: measuring indicia of physiological and cognitive states of each of the plurality of subjects; communicating the indicia to a monitoring computer system; with the monitoring computer system, comparing the indicia with one or more models of previous collaborative performance of one or more of the plurality of subjects; and with the monitoring computer system, employing the results of the comparison to communicate commands or suggestions to one or more of the plurality of subjects. In the preferred embodiment, measuring is done by one or more of: electroencephalography devices; electro-oculography devices; electrocardiography devices; respiration rate devices; galvanic skin response devices; blood pulse volume devices; electromechanical motion sensors; and accelerometry devices. Comparing comprises applying over time a sliding window Fourier transform to one or more of the indicia. One or more of the models in the comparing step comprises a self-organizing map, such as a self-organizing map of a single subject of the plurality of subjects, a self-organizing map of multiple subjects of the plurality of subjects, and/or a self-organizing map of all of the plurality of subjects. Commands or suggestions can be automatically communicated, or a monitoring human can view one or more of the indicia and/or one or more results of the comparison to a monitoring human who initiates commands or suggestions. Additionally, the system can communicate visual images of one or more of the plurality of subjects and display the visual images to the monitoring human.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

The patent or application file contains at least one drawing executed in color. Copies of this patent or patent application publication with color drawings will be provided by the Office upon request and payment of the necessary fee.

DETAILED DESCRIPTION OF THE INVENTION

The present invention is of a method and apparatus for real-time human collaboration monitoring and, preferably, intervention. Members of the group are individually monitored using one or more of the following non-invasive techniques: electroencephalograph (EEG, brain); electro-oculography (EOG, eye); electrocardiography (ECG, heart); respiration rate (lungs); galvanic skin response (GSR, skin); blood pulse volume (BPV, cardiovascular system); electromechanical motion sensors (somatic systems); and accelerometry (preferably wrist(s) and head). Sliding window Fourier transforms (SWFT) can be used on collected data to visually portray changes over time (such as BPV data to characterize heart rate), and other physiological data can be visually characterized in the same fashion for real-time analysis by a human or machine group leader or observer. Self-organizing maps can also be developed in training for individuals or groups of individuals from a multi-dimensional collection of data, which then can be used to determine in real-time if an individual or group is straying from expected behavior.

Note that while the subjects preferably are human, the invention can apply equally as well to non-human subjects, such as dogs trained for a particular mission.

Figure 1:
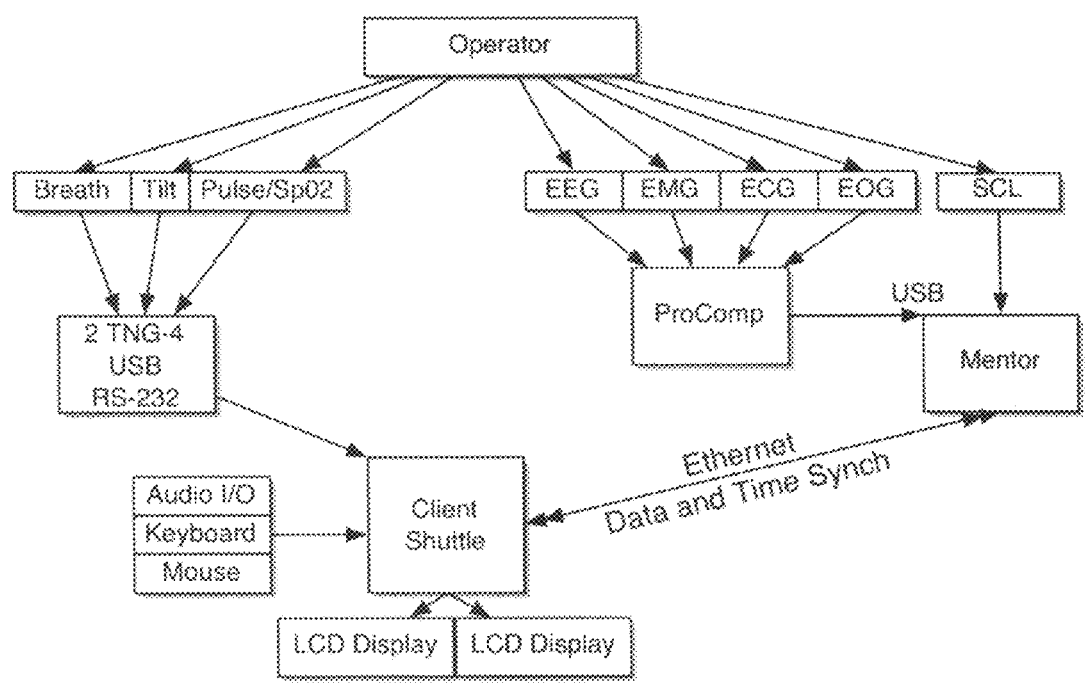
FIG. 1 is a block diagram of a preferred system according to the invention.

FIG. 1 provides a block diagram of an exemplary system according to the invention, in which an operator is monitored by a plurality of non-invasive techniques, receives direction from a client computer system (e.g., a Shuttle™ computer) with a display (e.g., an LCD display) and/or audio input/output unit. The operator's computer system is preferably in communication (e.g., by Ethernet or wireless connection) with a mentor computer which may or may not be monitored by a human. Data analysis computer software may be embodied in the client computer system, the mentor computer, or both, such as NeatTools™ or LabView™. Intervention software may similarly be on one system, the other, or both, and can provide commands or suggestions to the operator based upon results received from the data analysis computer software.

The invention preferably employs a sophisticated visual-programming and runtime environment known as NeatTools, available for download from www.pulsar.org. Unlike textual programming languages, NeatTools applications are developed by dragging, dropping, and interconnecting modules (visual icons) on the NeatTools desktop. Modules typically have a number of properties that can be modified by right clicking on the module and then adjusting parameters and other fields. Because NeatTools is multithreaded, the programmer can develop and edit an application, even while it is running and displaying data in real time. NeatTools is extensible, in that new modules can be written in C++ and loaded optionally at runtime as dynamically linked libraries (DLLs). A program generator to facilitate the writing of external modules is available at www.pulsar.org, as are documentation and representative application programs.

The preferred hardware of the invention employs MindTel TNG™ serial interface boxes (palm sized) that allow signals from sensors and transducers to be interfaced to personal computers, using NeatTools or other environments, such as LabView™. At the heart of each TNG interface unit is a PIC microcontroller programmed in assembly language that handles most of the functions of the device; because they are flash memory devices, they can readily be reprogrammed as needed. TNG-3B accepts signals from 8 analog and 8 digital sensors, and streams the data at 19.2 kbps. NeatTools includes a TNG-3 module to accept and distribute the signals. Standard sensors, mounted on cables with stereo or mono plugs, include photocells, bend and pressure sensors, rotary and slide potentiometers, and tactile switches. For use with TNG-3B or TNG-4, one can employ a 2 axis MEMS accelerometer/tilt-sensor.

TNG-4 is a serial interface with 8 analog inputs, 4 analog outputs, and 16 bidirectional digital lines. In addition, TNG-4 is extensible via its SPI port (Motorola's Serial Peripheral Interface that employs a synchronous serial protocol). Among the SPI extension boards developed to date are servo motor control (each board can control 8 servos and up to 8 boards can be daisy-chained); LCD display; keypad input (up to 8×8) and IR communication; vibrotactile control (up to 8 vibrator motors per board, which can be used for other pulse-width-modulation applications too); AC and/or DC relay control (4 per board; mix and match); temperature sensing (thermistor or thermocouple). There is also an electromyography (EMG)

board that connects to an analog input of TNG-4 and displays root mean squared (rms) values of raw EMG signals.

There are two distinct versions of TNG-4: streaming mode (like TNG-3B, but now duplex) and command mode; they differ only in the program in the respective PIC chip. In command mode, the computer issues specific byte sequences instructing the device how to configure itself and what specific data to accept or return. By repetitive issuance of such commands, the device can be made to stream in effect. Neat-Tools at present has a TNG-4 module for the streaming mode version of TNG-4 only; but it is easy to construct simple data flow networks to produce the required byte command sequences for specific applications. Command mode TNG-4 is well suited to work with handhelds such as Palm OS and Pocket PC devices, and other like personal information management devices.

A standard TNG-4 data acquisition device uses a PIC16F74 processor running at 4 MHz and communicates at 19.2 kbps. By increasing the processor clock speed to 12 MHz, one can increase the communications bit rate to 57.6 kbps. By utilizing either a PIC16F874 or a PIC16C774 processor one can increase the ADC bit resolution from 8 bits to 10 and 12 bits, respectively.

The increased ADC resolution comes at the price of having to transmit more data per acquisition cycle. At 57.6 kbps, 360 data packets (samples) per second can be transmitted when using ADC resolutions in excess of 8 bits. The standard 8-bit resolution protocol would allow 480 data packets (samples) per second at 57.6 kbps.

Concerning monitoring of respiration, the UFI Pneumotrace II respiratory band output is in the range −100 to +400 mV. The output signal can only drive input impedances in excess of 100 k$\Omega$ (>1 M$\Omega$ preferred). The Pneumotrace output signal is also AC-coupled with a time-constant in excess of 20 seconds. Optimally, two respiration bands should be used: one at the level of the navel and the other around the upper chest. The Respiration Amplifier preferably provides gain and filtering for up to two Pneumotrace respiratory bands and connectivity to TNG-4. The device is powered by TNG-4. The device has a frequency response of approximately 0.05 to 2 Hz. There is no electrical connection to the subject.

An IR Plethysmograph Signal Amplifier allows use of the Nonin $SpO_2$ sensors with TNG-4. The device powers the sensor and all TNG-4 to capture the blood volume pulse signal with appropriate amplification and filtering. There is no direct electrical connection to the subject with this apparatus. If $SpO_2$ is desired, the sensor can alternatively be attached to a standard XPOD module equipped with a serial-to-USB converter.

An SCL (skin conductance level) Device continuously digitizes the subject's SCL (skin conductance level) with at least 10 bits of resolution over a range of 0 to 100 micromhos (microsiemens). The device can be calibrated by commands from the host to switch in 0.1% precision resistors. Other features include a 12-bit DAC for zero suppression and a device to read ambient temperature (optional). The data rate (not baud rate) can be controlled over a limited range from the host. The default rate is 100 samples per second. The SCL device is preferably powered by a 9V alkaline battery. The device power is enabled by the assertion of DTR from the host interface (just like TNG-4). The battery-powered side of the serial interface is optically isolated from the host. To measure SCL, a constant 0.5 volt potential is applied to the subject by means of a pair of electrodes. Even so, the device presents much less of a hazard than a 9V alkaline battery.

INDUSTRIAL APPLICABILITY

The invention is further illustrated by the following non-limiting example.

Example 1

The invention was tested to explore its potential to improve the performance of small groups. The first phase of this project consisted of the development and construction of a testbed for exploratory analysis of small groups working in high cognitive load tasks. The system consisted of four computers to be used in the function of PALs (a dedicated personal appliance), and a fifth machine to serve as MENTOR (a group system architecture). Each of the PALs was equipped with an array of devices to collect physiologic and somatic data from a group of test subjects as they collaborated on a high stress, high cognitive load task. The task selected for the subjects was a "first person shooter" collaborative video game. Audio, video, and game scores were recorded as well.

Phase two of the project involved the collection and analysis of subject data. Four subjects participated in ten game playing sessions over a period of 3½ weeks. The first session was a self-paced training session, after which the subjects participated in a collaborative group environment to win the video game. They were encouraged to collaborate with each other, talk, and plan. Over the course of time, the settings were changed on the video game to make it more difficult for the subjects to win. Throughout the exercise, the subjects were connected to a variety of physiologic and somatic sensors. Analysis of the data was performed concurrently and subsequently to the scheduled sessions.

The data analysis proceeded in the following manner. Videotapes were examined and events of special interest were noted. The video and physiological data were synchronized and video data were compared with heart rate data to see if any correlation existed with the events of special interest. The study culminated with the development of two unique self-organized map approaches to analyze the data: one to work on PAL, one to work on MENTOR.

The testbed comprised an instrumented collaboration station equipped with networked computers and interface systems for tracking four users simultaneously during directed collaborative activities. The system had the capability to simultaneously track and record multiple data streams from four individuals in a group collaborative. Each of the four participants has his own computer (PAL), suitable for taking part in specified group activities. The user interface comprised an array of physiological-sensors, electro-mechanical sensors, microphone, face camera, mouse, and keyboard. This allowed for the capture of physiological, somatic, audio, video, mouse click and keyboard data. The system incorporated a fifth machine (MENTOR), which allowed an observer to monitor data. The capability existed to analyze the data streams generated in real time.

The physiological data collected from the subjects included electrocardiogram (EKG), electromyelograph (EMG), galvanic skin response, respirometer (breathing), and pulse oximeter. All sensors except the respirometer and pulse oximeter (blood pulse volume, BPV) were attached using skin electrodes equipped with adhesive. The respirometer measurement apparatus was a Velcro fitted chest strap. The BPV was a clip that fit on the ear just above the lobe. Two EMG sensors were used, one on the arm to capture wrist and hand movements, the other on the upper cheek to acquire facial expressions such as grimaces. The EKG sensor was attached to the chest directly over the sternum.

Three accelerometers were used to record body movement. Two were placed on the back of the hands. These sensors were attached using standard first aid tape. The remaining accelerometer was taped directly to the earphone headset to record head movement, eliminating the risk to the subject of hair loss from tape removal.

The system was also equipped to record electroencephalogram (EEG) data, which provided information on brain activity. However, EEG data was not collected in this study.

Data containing information on electrocardiogram, electromyelograph, and galvanic skin response were stored on the MENTOR machine. Accelerometers, respirometer, and pulse oximeter information were gathered using MindTel TNG devices and stored on the individual PAL machines. There was some sample jitter present in the physiological data. For example, the data stored on the PAL machines had an average sampling rate of 22.6/s, or 44.2 ms between samples. But at times the machine recorded duplicate time stamps (two samples with different values occurring at the same moment), and at other times samples may have been 100 ms or more apart. However, for this application the data was oversampled, and the jitter was negligible. In general, the data values recorded for duplicate time stamps were different, which means they were actually recorded at different times. This implies that the device was recording time stamps incorrectly. However, there is not enough evidence for one to that the device is taking evenly spaced samples. This uncertainty in sampling interval must be taken into account when analyzing the data.

Due to the uncertainty involved in locating the data to a precise point in time, a time window method of signal analysis was adopted. If this type of analysis was used, the error was acceptable, provided the cumulative error over a 45 minute session was one second or less.

The running game scores were recorded on VHS via a video feed from MENTOR, which was logged into the game as an observer. The start and end of each session was captured as well. Video data of subject faces and speech was displayed and collected on VHS using a quad splitting device. Thus, all four subject faces would appear on a split screen at the same moment, allowing for analysis of subject speech and facial expressions. The video was not time synchronized to the physiological data. Therefore, once each session, the subjects were asked to make a precise movement at the count of three, allowing that moment in the data to be pinpointed on the video. The time synchronization can also be double checked by noting the amount of elapsed time between the start of the data recording session, and the start of the first game (both events are recorded on the MENTOR video).

In July, five test subjects were recruited. A higher percentage of men volunteered for the experiment than women. For the scope of this work, it was desired to recruit subjects who had never played the game used before, nor many such games in general. Ten sessions were conducted over the course of 3½ weeks, each lasting approximately one hour. The potential recruits were each shown the test setup and equipment and allowed to review a consent form explaining the risks of the experiment before giving their agreement to participate.

The final subject group was all male. This was not the intent of the authors, and several women did volunteer for the study. However, the final selection was dictated by the schedules of the subjects. An additional unplanned outcome of the subject selection was that all five subjects knew each other before the study began. They were requested not to discuss the game or to play it outside of sessions. The ID numbers of the five test subjects are: 4564, 4859, 6068, 7621, and 8913.

It was desired to have a group activity for this experiment that would be interesting, engaging, cooperative with individual and group outcomes, and would elevate the stress level of the subjects without requiring them to share personal information. It was decided that a first person shooter video game used in the multiplayer mode would possess all these qualities. Rainbow Six 3: Raven Shield (R6)™ was selected for this study. This is a commercially available first person shooter game, with multiplayer capability. The game can be configured many different ways. The subjects can be teammates, or adversaries. It was desired to have the subjects serve as teammates, and work together to free hostages. The mission required the players to kill computer-generated terrorist characters and protect hostages, all with little or no team losses. The terrorists would shoot at the players, and they would also shoot a hostage if the cyber terrorists "detected" the close presence of the team. There were no safeguards in place to prohibit friendly fire.

There were two ways to lose the game. The first was that the entire team could be killed. It was also possible to lose the game if someone killed a hostage. Most likely it was the terrorists who killed the hostage, but it was also possible for team members to shoot a hostage accidentally. There was only one way to win the game: to kill all the terrorists.

The first meeting was a training session. The subjects worked through a set of preprogrammed training exercises at their own pace. They did not interact with other subjects during the training phase. At session 2, the subjects began to play the game interactively in multiplayer mode, working together to achieve an objective. As the subjects learned the game and became accustomed to working together, the game settings were adjusted to become gradually more difficult. An outline of the difficulty level for the 10 sessions is included below.

Session 1: All subjects were trained, at their own pace.
Sessions 2-6: "Peaks" Scenario (outdoor, daylight)
Session 2: Recruit level, 5 terrorists
Session 3: Recruit level, 15 terrorists
Session 4: Veteran level, 10 terrorists
Session 5: Veteran level, 15 terrorists
Session 6: Elite Level, 10 terrorists
Sessions 7-10: "Warehouse" Scenario (indoor, night)
Session 7: Veteran level, 10 terrorists
Session 8: Veteran level, 15 terrorists
Session 9: Elite Level, 10 terrorists
Session 10: Elite level, 10 terrorists Multiple runs of the game were played in each session of nominally 45 minutes duration. However, if the running session time was greater than 43 minutes, another round of the game was not played. In addition, if play ran over 45 minutes, the subjects were allowed to finish playing their current game. The game was set to reload after every team win or loss. The players had between 30 and 45 seconds (depending on the session) between games to change their weapon selection. In a typical 45 minute session, the subjects would run through the game approximately nine times. Some sessions had fewer runs of the game, some had as many as eleven. Variables determining game time were ability and difficulty level of the game.

Once a team member was "killed" in the game, he would not be allowed to speak to other members until that round of the game was over. However, a dead subject could "ghost" around the scene, moving to various points as a spectator to observe the action that was still continuing.

In order to observe changes in the group dynamics, it was desired to substitute team members at pre-selected intervals. The plan was for the first four team members to be selected at random from the five volunteers. The emerging group dynamics of the data would be analyzed, and a based on observations a team member would be substituted out after session 6. The fifth team member would be substituted in and allowed to play sessions 7-10. Subsequent to session 9, one of the original team members would be rotated out, and the team member who sat out sessions 7-9 would be substituted back in for the final session. However, a schedule conflict emerged after the start of the study, which caused one subject to be unable to attend sessions for an entire week. Since there were less than four weeks to complete all ten sessions, there was no room available in the calendar for rescheduling three entire sessions. Thus, this subject was allowed to be the one to sit out sessions 7-9.

The attendance of the five subjects is listed below:
Subject 4564 was present for sessions 1, 7-10.
Subject 4859 was present for sessions 1-9.
Subject 6068 was present for sessions 1-6, 10.
Subjects 7621 and 8913 were present for all sessions.

The initial examination procedure for the data included four approaches. First, discrete observations were made of the group by the principal investigator, who was present in the room at all times during sessions. Second, a quantitative analysis of individual and group performance was executed using the recorded game scores. Next, each session's face videotape was analyzed to identify examples of cooperation, conflict, leadership, and other critical events. Finally, the physiological data was analyzed and correlated with the other observations.

While the primary focus of this study was physiological data, it was necessary to observe the social interactions of the group to put the physiological data into perspective. As such, this section is not a detailed scientific social analysis, but rather a series of discrete observations regarding group dynamic trends.

The group at the first cooperative session (session 2) consisted of four men with a variety of different skills and prior experience with video games. By the end of this session, a leader began to emerge, subject 8913. In session 3, the other subjects began following the leadership of 8913 and asking him for advice. Interestingly enough, subject 8913 was usually the first team member to be killed in these early sessions. He was not an unskilled player (see the scoring section below). He was taking more chances than the other players and thus placing himself at greater risk. During the periods when his character was dead, he was searching around the scene (as a ghost) and looking for the vulnerabilities in the game. By session 4, 8913 was devising and executing elaborate cooperative battle plans with the assistance of the other subjects, and continued to do so throughout the remainder of the sessions.

However, another player also served as a leader and was less vocal, subject 7621. This subject admitted to having prior experience with first person shooting games. By session 5, subject 7621 was planning tactics with 8913 and coming into occasional conflict with him. By the beginning of session 6, a metamorphosis was occurring. The group was no longer one team, but two. Subjects 8913 and 7621 were each in charge of one of the other players (which player varied from session to session), and began calling themselves the alpha and bravo teams. Subject 8913 still had control of the group, but 7621 would function rather autonomously with his own two-person team in a different part of the playing field. He was typically after an important, but different, objective. In addition, if one of the less experienced players had a question on how to use equipment, etc., it was generally 7621 who took the time to calmly explain and instruct.

Subjects 6068 and 4859 generally assumed following roles, but as the sessions progressed they made more suggestions as they became more comfortable with the game. Neither one issued many commands. When subject 4564 replaced subject 6068, it appeared as if the group dynamics might change. From his introduction, 4564 made many strategic suggestions, took risks, and seemed to be trying to act as a full contributing member of the team. Perhaps he would have emerged into a leadership role had he been introduced to the game earlier. By session 7, the other players were quite versatile in the game logistics (moving, throwing grenades, etc.), while 4564 was still trying to learn. This put him at a disadvantage. However, it was observed that in the few cases in sessions 7-10 when both 8913 and 7621 died early in the game, 4564 assumed the leadership role over the remaining player.

A complete log of subject scores and game outcomes appears in A. Doser, et al., supra. There were several variables involved in the analysis of the game performance. As mentioned before, the sessions were designed so that R6 became progressively more difficult. In addition, a new player was added and old players were rotated in and out. In session 1, a training exercise was executed, and no scores were taken. Scores were recorded beginning with the first collaborative exercise, session 2.

There are two performance parameters of interest that can be measured quantitatively from scores alone: group performance and individual performance. Group performance is measured as the number of wins/losses per session. Individual performance is measured here in two ways: number of kills, total time alive per session. Group performance will be discussed first.

In a typical 45 minute session, the subjects would be able run through the game nine times. One session had 11 games, two sessions had only 6. During session 2, the subjects were doing well, winning 9 of 11 games on the easiest game setting. As the sessions went on, more terrorists were added, and the difficulty level increased. The subjects began to falter, then recover. Their best performance was achieved in session 5, winning 9 of 10 games. Session 5 was Veteran (mid-level), with 15 terrorists. In session 6, the elite level was applied, and the subjects won only one game. In session 7, a new, arguably more difficult map (location) was applied. The subjects won only one game in the last four sessions. Sessions 7-10 included the introduction of a new player and the rotation in and out of two veteran players. One cannot say with certainty that the group performance diminished due to group dynamics, or due to the increased difficulty level of the game. However, some subjects did comment that they felt the setting of the game was too difficult for their skill levels in the later sessions.

The subjects with the greatest average number of kills achieved them in the least average amount of time. Subjects 8913 and 7621 were the members of the group most often taking leadership roles. As such, they put their characters in more danger than the other subjects. This allowed them the most target opportunities, but also more chances for their characters to be killed.

The group seemed to adapt and perform well in spite of the increasing difficulty levels of the game in the first half of the study. In the second half of the study, the group's performance took a major downturn. It is unknown if this reduction in performance was due solely to the difficulty level of the game, or also to the change of players in the last half of the sessions. In individual results, it was noted that the players with the greatest average number of kills were also generally the first ones to have their characters killed in the game.

Each session was videotaped, using a quad-splitter device. This allowed all four subject's faces to be displayed, simultaneously, on one screen. The audio quality of the recordings was quite poor, but in general it was possible to understand the speech of a subject. The video of each session was analyzed to identify examples of cooperation, conflict, leadership, and other critical events. Examples of statements demonstrating items such as cooperation and conflict were noted from the video, and logged manually according to type and time.

For the purposes of this study, statements of interest were grouped into the following categories. Since many statements were inaudible, it was not felt that a running count per session by person would not be very accurate. Thus, statements of interest were noted solely to provide correlation to the physiological data.

Types of statements noted:

Leadership (L): For example, "Stay behind me."

Following (F): An example would be, "Where do you want me to go?"

Cooperative (CO): For example, "I've got your back."

Conflict (C): For example, "I don't think that's a good idea."

Reporting (R): For example, "This area is secure."

Inaudible (I):

Primarily, events surrounding L, F, CO, and C statements were examined. Reporting statements, while they convey information, were not generally associated with any observable change in the physiological data.

There is some ambiguity surrounding statement classification. The same statement could be classified different ways, depending upon the context. For example, the statement, "I'm approaching the house," would generally be considered to be a reporting statement. However, if it follows another statement such as, "They're shooting at me in front of the house!" then, "I'm approaching the house," would be classified as cooperative—since one subject was running to the aid of another.

Once statements of interest were located in the video data, they were compared to the same interval of time in the physiological data, to see if the subjects exhibited any noticeable reaction. This approach is next described.

As just mentioned, statements of interest were located in the video data in order to correlate these events with the physiological data. The point being to see, for instance, if a subject makes a statement such as "Follow me," if it results in any reaction in physiological data among the subjects, and to see if that reaction changes over the course of the sessions. However, if there is a reaction in the data, is it due to the vocal cue, or something else? For example, suppose one subject says to another, "follow me," and the second subject's heart rate spikes to a higher level. Did his heart rate spike because he was given a command, or was it perhaps because he was taking hostile fire at the same moment? Without a camera recording what each subject sees on the screen, it is difficult to tell exactly what a subject is experiencing in the game at any given time. Even if the study had been equipped with such a capability, and one could tell he was being fired upon, one still cannot answer the question with complete confidence. One could only be certain he was reacting to "follow me" if one could confirm he was experiencing nothing else of consequence in the game at the time.

That said, one can attach a confidence level to each incidence of vocal data that is potentially associated with a physiological reaction. For the purposes of this study, these levels are called high, reasonable, and low confidence.

High confidence events:

One's death: just as one's body would have a stress reaction if someone pointed a gun at him in real life, most people tend to react strongly when their video personality is killed. It is fair to assume that if a reaction in the physiological data occurs that can be associated with a person's death in the game, that he is reacting because he got killed.

Death of comrades after one's death: After one is killed in R6, he becomes a ghost. He is no longer being fired upon. He is no longer shooting. He may become disengaged and start daydreaming. But if one of the group dies after him, and one sees a reaction in his data, it is assumed that reaction is due to the death of his comrade.

Conflict with eye contact: If two players come into conflict and have a discussion over an issue, and they are looking at each other for an extended period of time (not the computer), one can assume that any reaction in the data is due to the conflict. Similarly, one can draw the same conclusion if two players are looking at each other and cooperating to plan an attack.

Reasonable confidence events:

A physiological reaction in the speaker of most L, F, or CO statements: The reaction in a bearer of a statement can be said to be more reliable than in the recipient of a statement. Why should this be the case? The reaction of the speaker that is observed is generally not a reaction at all, but a precursor. Often, a reaction in the data can be seen just before the statement is made. The subject is assessing whether to make the statement, because it may involve a risk. For example, it was witnessed several times over the course of the sessions that one subject would say, "I need some help down here!" This statement would be followed by a pause of 5-10 seconds, then another subject would say, "I'm on my way." In many cases, the second statement would be preceded by a spike in the heart rate and respiration of its speaker. If such an association occurs, one can be reasonably confident of its source, provided another event does not occur within close proximity of the precursor.

Low confidence events:

A physiological reaction in the recipient of most L or CO statements: As explained previously, it is very difficult to determine if a recipient is reacting due to the statement, or some other event in the game.

Death of a comrade while one is still alive: Often, a subject is also sustaining heavy fire when his partner is killed. In addition, he may be so busy he does not even realize his buddy has been killed for several seconds. Drawing a connection in this case is difficult. The exception is if the survivor is the last one left standing. Many subjects do exhibit a strong reaction when they find they are all alone on the mission, as will be shown later.

Analysis of heart rate variations can illuminate much about a person's activity and stress levels. In this study, heart rate and heart rate variation could be gleaned from two separate sensor systems: the blood pulse volume sensor (ear clip), and the EKG chest electrode sensor suite. In this section, analysis using the BPV sensor will be discussed.

Data from the BPV sensor ear clip could be used to track variations in a subject's heart rate. The device that drove the BPV sensor in this experiment had a sampling rate that averaged 22.6/sec, although as mentioned earlier in this report, there may have been some timing jitter that affected the true sampling rate at any given moment. If it is assumed the true sampling rate is 22.6 Hz, according to the Nyquist sampling theorem, in an ideal case, frequencies up to 13.3 Hz can be captured without aliasing. Under normal circumstances, if a person is sitting, it is reasonable to assume his heart rate will not vary much outside the interval of 1-2 Hz (60-120 beats/minute). Thus, the sampling rate is more than adequate, and the jitter should not present a significant problem if frequency analysis techniques are used.

To examine the change in heart rate in the BPV data, a time/frequency technique was used. A sliding window Fourier transform (STFT) was applied. An STFT works by taking Fourier transforms of data over short periods of time using a window, sliding the window, and repeating. Thus creating chunks of Fourier transforms. If these Fourier transforms are attached on the time axis, one can start to get a feeling of what the frequency content of a signal looks like at different periods of time.

Unfortunately, there is a trade off between time and frequency resolution. It is mathematically impossible to simultaneously achieve both great time and frequency resolution. Wavelet transforms can be useful, as they allow one to sacrifice resolution in some parts of the spectrum and save it in others. In the BPV data, the area of concern is only a small part of the spectrum, where both time and frequency resolution are desired. This makes a conventional wavelet impractical. While a custom made transform could be designed to meet these needs, the time available in the project was insufficient for its development. Thus, a compromise was made. Since, for short periods of time, there was uncertainty in the time stamps of the data, a decision was made to allow the time resolution to be 5.68 sec, with a 50% overlap between windows. Thus, a frequency contribution at 5.68 sec would represent time between 2.84 sec and 8.52 sec, a frequency component at 8.52 sec would represent time between 5.68 sec and 11.36 sec, etc. In other words, although the entire time period would be represented, it would be impossible to pinpoint any moment in the spectrum except to say that it happened sometime in a 5.68 sec interval. Since heart rate cannot change instantaneously, the resolution seemed adequate. In addition, statements made by subjects may last several seconds. The corresponding frequency resolution was 0.09 Hz (thus, there would be approximately 11 frequency bins covering the space of interest between 1 and 2 Hz). In other words, a change in one vertical frequency bin represents a heart rate change of approximately 5.4 beats/minute.

Often, a burst-like phenomena will appear in the STFT, where a signature appears to be smeared all over the entire frequency (vertical) axis. This artifact can be explained. When a subject reaction is accompanied by a sudden change in intensity, it sometimes is recorded as a DC shift in the data. Essentially, it is a step function (positive or negative) added into the time domain data. It is a fact of Fourier analysis that a discontinuity in a time signal has a component over the entire frequency plane. Although the largest component is at DC (0 Hz), influence can be witnessed at other frequencies.

Figure 2:
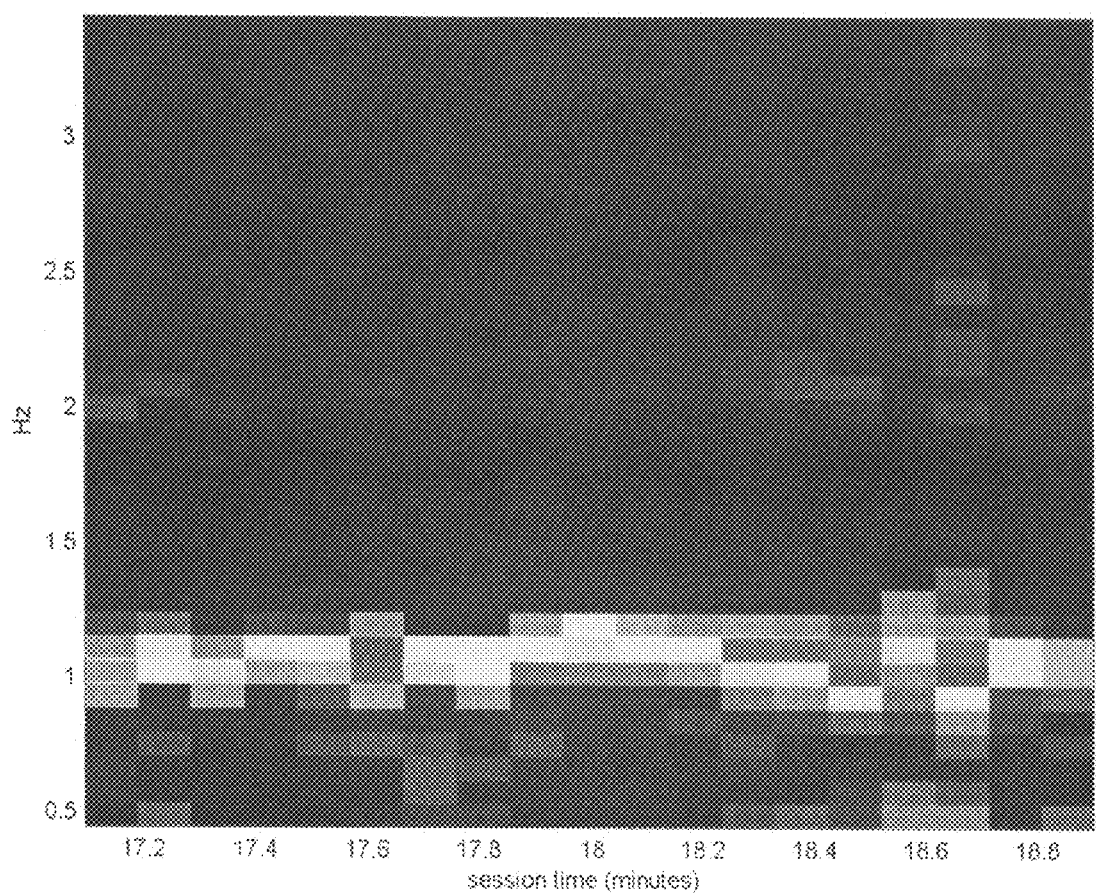
FIG. 2 is a blood pulse volume (BPV) signal from a subject processed by sliding window Fourier transform (STFT) according to the invention.

FIG. 2 displays the STFT of a typical BPV series for a subject during the game. Note the strong horizontal signal at approximately 1 Hz. This is the subject's heart rate, which seems to be varying in intensity with the events of the game, but there is not much frequency variation in this interval. One can observe much weaker signals at 2 Hz, and 3 Hz (light blue). These are harmonics of the heart rate signal at 1 Hz. Harmonics are an artifact of the Fourier transform, and do not represent error. Other lightly shaded pixels in the figure are the result of noise sources.

As mentioned previously, videos were viewed and statements logged for the purpose of seeing if any correlation existed between the voice and physiological data. This section is a qualitative one, and will provide supporting evidence for a subsequent section on self-organizing maps.

Figure 3:
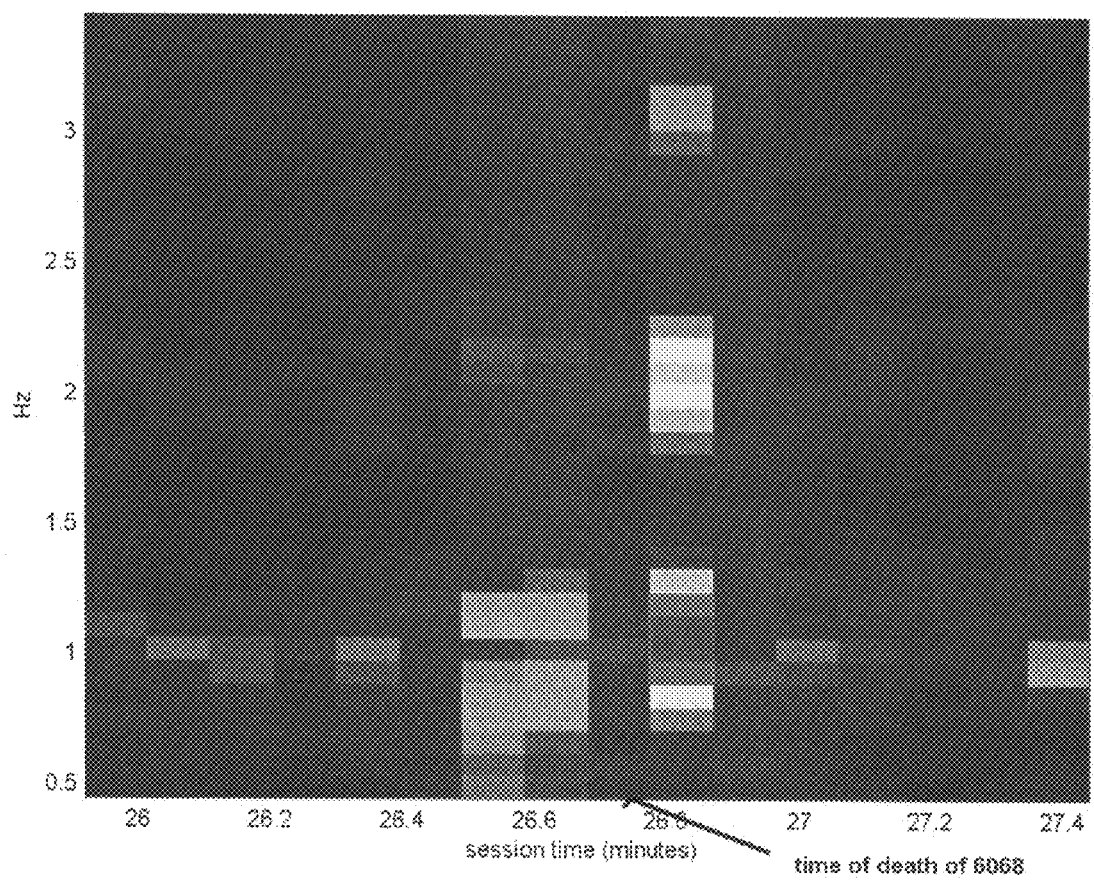
FIG. 3 is such a BPV signal showing reaction of a subject to his character's death in a game.

The examination began with the high confidence events, starting with the death of one's own character. FIG. 3 is an example of a typical response observed in the BPV data when a subject's character dies in the game. In general, a reaction is not observed until 2-5 seconds later, that is, the next time bin.

Note the strong reaction in heart rate intensity after the subject realizes his character is dead, as noted by the dark red pixels just before 27 minutes. The artifact can be observed in the harmonics as well. Some subjects reacted to their character's deaths with changes in heart rate intensity, an elevated heart rate, or both. It was interesting to observe that one subject, 7621, seldom produced a change in heart rate or intensity when his character was killed. However, it was noted from the videos that this subject usually did throw his head back when he was killed in the game. Thus, when his heart rate data was combined with accelerometer data (see the SOM section below), some reaction could be observed.

Another high confidence event examined was the reaction of a subject to his comrade's death, after the subject has died himself. At the beginning of the sessions, the typical observation is that after one's death, one would have no reaction upon the death of a comrade. When the data from the early sessions was first examined, it was determined that, in general, subject 8913 did not react to a comrade's death in the way illustrated above. Subject 8913 continued to react to events in the game after his character was dead. He experienced heart rate changes after the deaths of his teammates.

Since subject 8913 emerged as the leader of the group, does that imply that reacting to the experiences of others is a characteristic of a leader? However, consider the following observation. As the sessions progressed, on occasion other subjects began reacting to comrade's deaths in the same way as 8913. One conclusion is that the subjects are beginning to act cooperatively, and to behave like a team.

Other conflicts and cooperative events were studied in the data. They do not always invoke a reaction in the data. Different subjects reacted differently. Subject 8913 reacted very little to conflict events. Subject 7621 reacted more strongly to conflict events than he did to his own death events. Subject 4859 reacted more strongly to cooperative events. Subjects reacted differently at different times, most likely due to the seriousness of the event.

It was hoped from this study that physiological data could be used to identify signatures of group learning and cooperation. But how do subjects function due to lack of cooperation? There was a multitude of data available from the study that included cases where one subject was the surviving member of the team, and often carried on for several minutes on his own. As nothing was said during these intervals (subjects were not allowed to talk after their character's deaths), it could be assumed that any reaction from the survivors was due to the events in the game. It was decided to examine heart rate data for signs that a subject may be experiencing agitation due to the lack of cooperation from his comrades.

The heart rate of subject 4859 was observed as he worked alone in the game for approximately 90 seconds prior to winning. A steady rise in his heart rate occurred after the death of his teammate. The rise was even more apparent observing the first harmonic at 2 Hz.

By far, subject 4859 spent the most time as the survivor. Of the others, it was almost never the case that they were left standing alone for more than five seconds. Of those games when another survivor was left standing 30 seconds or more, similar gradual heart rate elevations were witnessed in his data.

An interesting phenomena was noted in session 8. 7621 was alone in the game for 42 seconds. Not only did his heart rate rise, but the heart rates of the other subjects, who were dead, rose steadily as well. For the specific period of time, 7621's data and the data of one other subject are plotted below. It seems too, that this artifact may be an indication that later in the study the group was functioning more as a team.

This section was an exercise to determine if correlations existed between what was said in the video data and reactions that were observed in the physiological data. In many cases, no reaction was observed in the physiological data. But in the events discussed here, if there was a reaction observed, it was reasonable to believe it was due to the event in question.

Additionally, the following trends were observed. In early sessions, subjects would become detached after their characters were killed, and only the leader, 8913 would remain engaged in the game. This was illustrated by the fact that the subsequent death of a comrade would result in a spike of 8913's heart rate. As the sessions progressed, this artifact was sometimes noted in the other subjects as well. It is especially true of subject 7621 (see the section on SOMs below). This behavior could indicate a possible signal of emerging group cooperation, or perhaps the subjects are beginning to emulate the reactions of the group leader.

When a subject is the last survivor in the game, it was noted that his heart rate began to gradually climb. Such was the observation in all subjects who managed to live 30 seconds or longer as the last survivor. In early sessions of the game, only the survivor's heart rate would climb. However, as the sessions progressed, it was noted in one case the dead character's heart rate would climb along with the survivor's. This could also indicate a cooperative trait.

When responding to various statements in a variety of situations, the subjects reacted very differently. Subject 8913 reacted very little to conflict events. Subject 7621 reacted more strongly to conflict events than he did to his own death events. Subject 4859 reacted more strongly to cooperative events. It was observed that subject 6068 reacted more to the start of a new game than anything else. Subjects reacted differently at different times, most likely due to the seriousness of the event. The conclusion is that all subjects are different, have different motivations, and there is no single metric that can be used to describe their individual data. While a discussion of heart rate analysis can be demonstrative, a more concise approach is required. Such an approach is discussed in the section on self-organizing maps.

A self-organizing map (SOM) can be helpful to spot correlations in a set of data. SOMs were developed by Teuvo Kohonen, in the early 1980's. T. Kohonen, *Self-Organizing Maps*, 3d ed. (Berlin, Springer-Verlag, 2001). SOMs are similar to neural networks, in that they are used in pattern recognition and classification. Unlike neural networks, SOMs are based on the principle of competitive learning. Over the course of training, by means of positive and negative lateral interactions, one cell becomes sensitized to a region of input signal values, and suppresses the sensitivity of the cells around it to the same input. Thus, each cell in the network is activated by a different constellation of sensor input values. The Self in Self Organizing Maps refers to the fact that the network trains itself, without any preconceived ideas of what the final outcome should be (unlike many neural networks).

Much of the SOM's power lies in its ability to reduce the dimensionality of an input vector space, while still retaining the distance relationships within that space. For instance, it is possible to reduce a 50 dimensional space down to two dimensions, and still be able to classify the data using a SOM. For this reason, SOMs generally do not provide a 1-1 mapping, with the result that more than one combination of inputs will activate the same output cell. However, if one wants to use a SOM for classification or to identify trends in data, this does not present a problem. In a classification application, one generally wants to have many inputs be represented as a single, or at most a small cluster, of outputs. A SOM must be presented a great deal of data in the training phase to achieve satisfactory results, not a problem in this study. The computational costs of a SOM is incurred in the training phase, with very little computation required to classify new data as it becomes available. As such, SOMs are suitable for near real time applications.

In the following sections, SOMs are trained, both for individuals, and for the unit as a whole. This task was taken to fit in with the concept of what roles PAL and MENTOR might play in the future, and to demonstrate that each approach has its own merit and applicability. Ideally, the methods should be used concurrently.

In keeping with the concept of PAL, the decision was made to train a SOM for each subject. As was shown in the previous section, every subject reacted differently under varying situations. Due to the uncertainty surrounding the true sampling interval in the TNG data, and the fact the EKG, EMG, and GSR data were sampled at a different rate, only the data collected by the TNG machines on the PALs (respiration, BPV, and accelerometer) were used to train each SOM. Since additional data other than BPV was used, an event that created a low stress level when only BPV data was analyzed would not necessarily map to a low stress level in the SOM.

A free version of a MATLAB SOM toolbox, developed by the students of the SOM inventor, was available to download without licensing restrictions at Helsinki University of Technology www.cis.hut.fi/projects/somtoolbox. The Helsinki SOM toolbox was found to be adequate for the scope of this project and was incorporated into the algorithms developed here.

In the previous section, the use of STFT time/frequency techniques seemed to unearth some characteristics of the physiological data and make them visible to the human eye, the SIFT was used to populate each SOM, as well. The vertical elements of the STFT were important in this endeavor. Each data file, when processed through the STFT in the manner described above, contained approximately 500 time bins and 129 frequency bins. Duplicate this number for each parameter (BPV, respiration, etc.). Each training vector to the SOM consisted of 17 parameters. Values 1-13 consisted of a subset of BPV STFT information. Frequency bins 11-23 were used, which represented values of approximately 0.9 Hz-2 Hz (54-120 beats per minute). Only magnitudes of the Fourier transform were included, the phase data was disregarded. For the respiration data, only the value and location of the highest magnitude frequency bin were included. For example, suppose the highest value for a given time bin occurred at 0.7 Hz and had a value of 0.3. The parameter entries would then be 0.7 and 0.3. The question remained of what to do with the accelerometer data. It was observed that while playing the game, contact with the mouse and keyboard required a subject's hands to be quite stationary. However, it was observed that head movements were quite common, mostly side-to-side. Therefore, x-axis accelerometer input was used in training the SOMs. Similar to the respiration data, the location and magnitude of the largest component for each time bin were included in the data vector. Thus, each training vector included 17 elements: 13 from BPV, 2 from respiration, and 2 from x-axis head accelerometer. A typical 45 minute session would provide approximately 500 training vectors.

One session of data was used to train the SOM for each of the five subjects. In order to observe trends developing over the course of the study, it was desirable to select a session which was somewhere near the halfway point. But in order to have the SOM experience the full range of data, it was necessary to select a session where the subject cooperated in several battle plans, experienced conflict, demonstrated leadership and following roles, and was killed multiple times. For subjects 4859, 6068, and 8913—session 6 was used. For subject 7621, session 4 was chosen. Since subject 4564 was present for only 4 sessions, the data used for his training set was from session 7. Once the SOM for each individual was trained, data from other sessions could be fed to the map, in order to search for evolutionary trends in the data.

The dimension of each SOM was selected by the algorithm based on the eigen values of the data. As such, the SOM for each individual was a different size.

Figure 4:
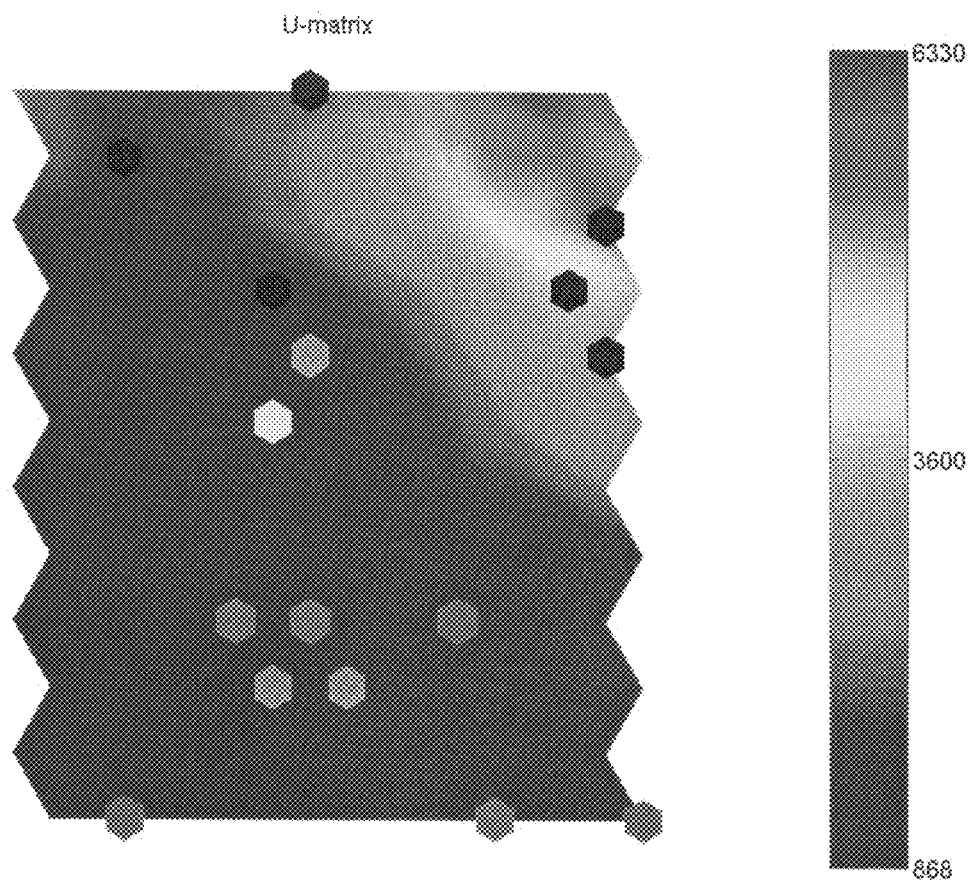
FIG. 4 is a U-matrix for a subject's Self-Organizing Map (SOM) generated according to the invention for one experimental session and showing events of interest from another experimental session.

A SOM was trained for each subject, based on the data from one session. Events of interest from the video were located in the data and mapped on the SOM. FIG. 4 is an example of a trained SOM for subject 4859. What is displayed is the Uniform Distance Matrix, or U-Matrix. The U-Matrix represents the distances between data elements in the input vectors. Blue areas represent where the data is close together in feature space, red colors represent data that is far apart. Generally speaking, a vector that maps to the red area would indicate a period of time where the subject was under high stress (high heart rate, high respiration, head movement). Consequently, in this case, a vector that mapped to the lower left corner (blue region) would indicate that the subject was quite calm.

Next, events of importance from the video were located to a certain point in time on the data and sent through the mapping process. For the training data, the results are also displayed in FIG. 4. First of all, it should be noted that a SOM does not provide a 1-1 mapping, meaning that several data vectors may map to the same location. Even though there were five occasions where comrades were killed after subject 4859, they map to only three points in the data (red). Note how, in session 6, the subject seems to be very stressed by his character's death events (black). He is not very concerned with the deaths of others (red). By this session, he is quite comfortable with the execution of battle plans of others (green). New game starts (pink) were included in this set, as some subjects display much stress at the start of each new game. However, as can be seen here, 4859 is not one of those subjects. On the other hand, events where he comes to the aid of others or has conflict with them (blue and yellow), give him moderate stress. In session 6, one would have to say that the events that bother 4859 are his character's death, conflict, and coming to the aid of another (cooperation).

What, then, of the large red section in the upper right corner that represents the highest stress level, yet has virtually no points located there? Which events cause so much stress as to be mapped to this region? In an off-line exercise, the generating data was plotted point by point to see which points in time were "red points", and compared with the video and game data. This region was found to correspond to a point of time in the session where no words were spoken between subjects, and shots were being fired.

What of the important events from other sessions? Syncing events from the video to the physiological data can be a painstaking process. Time permitted the analysis of three sessions only for most subjects, including the session where the SOM was trained (ideally one of the middle sessions). The other two sessions were one selected near the beginning of the study, and the last session where the subject participated.

Figure 5:
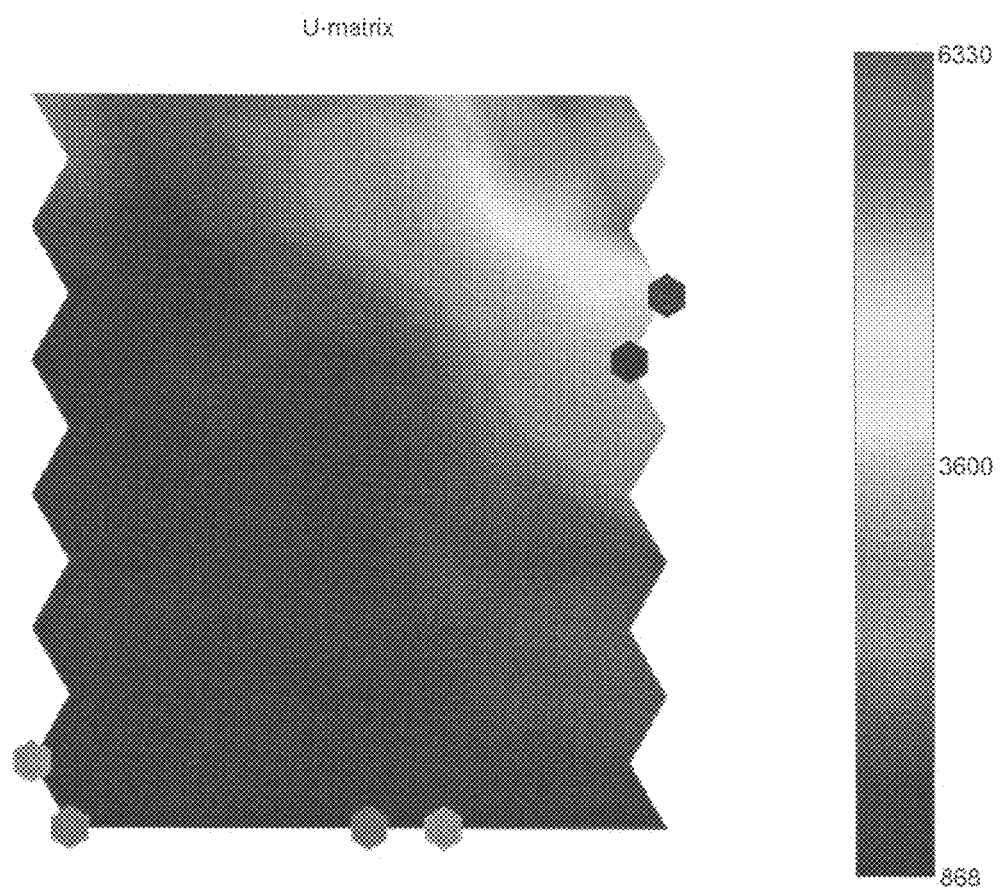
FIG. 5 reverses the roles of the two sessions in FIG. 4.

FIG. 5 is an example of the subject data from session 3, plotted on his mapped trained from the session 6 data. This way, one can make a direct comparison between the two sessions. Unfortunately, MATLAB only provides seven colors for plotting points on a map, not enough to capture all events of interest. In the figure below, instead of representing a plan execution, green represents uttering a following statement (such as "Which way do you want me to go?").

Much of the events from session 6 were present here, but there are some additional events, and some missing. In session 3, the subject was killed only once, and there were no occasions where a comrade was killed after 4859's death. There were no cases where 4859 was in conflict with anyone. However, he did issue commands or leadership statements (dark blue), and statements indicating he was in a follower position (green). Recall, this data is three sessions earlier than session 6. Note how uncomfortable the subject seems to be with issuing commands (dark blue), yet how comfortable the subject is with being a follower (green). At this point in the sessions, although a leader (8913) was emerging, the hierarchy of the group had not yet been established. In this session, 4859 spent much time as the lone survivor (see figure below), and occasionally won the game in that position. Thus, by the end of the session, he began to feel confident of his skills and started to issue commands to the others in the group. Interestingly enough, 4859 was not observed to issue another command until session 8, after the introduction of a new test subject.

In session 3, 4859 was the lone survivor on two separate occasions, for a total of nearly three minutes. It is interesting to note, that under such circumstances, 4859 exhibited high levels of stress.

The participation of this test subject did not extend to the end of the study. Therefore, the final session where his data was examined was session 8. The subject still felt quite comfortable with being a follower (green), and not as comfortable with issuing commands (dark blue). There were no occasions in session 8 where a comrade was killed after 4859 in the game.

Although a thorough examination of all the sessions might provide further revelations, the examination of the data presented here for 4859 would seem to indicate that very little change in the subject's reaction was noted throughout the course of the study. This was not the case for every subject. However, a careful review of the data here seem to indicate that the responses noted by 4859 are consistent with those of a follower.

Subject 8913 emerged as the leader of the group. His data from session 6 were used to train a SOM. That SOM was later used to chart 8913's data from session 3 and session 10. Through the entire course of the study, subject 8913 was not observed to make a single statement consistent with a follower. However, it is not impossible that there may have been such a statement imbedded in the video data which was inaudible to the observer.

Subject 8913 was very vocal, and generated many statements of interest. Because of this, it was necessary to show his data over many different plots, as some data would plot to the same points as others and would eclipse them. The SOM was a different size from the SOM of subject 4859. The size of each SOM is based on the eigen values of the data set. Different individuals have different sized SOMs.

As noted in a previous section, subject 8913 takes note of the deaths of his comrades (red), exhibiting maximum stress in one case. In session 6, in general, he shows more stress to the reaction of a comrade's death than he does from his own (black). In addition, 8913 seems to be very concerned about conflicts he has with others in the group (yellow).

Subject 8913 exhibited a wide range of reactions to the same stimuli. However, in general he seemed to be more comfortable with issuing commands (dark blue) than with coming to the aid of others (light blue). At times the anticipation of the start of a new game caused him stress (pink). Some of this game anticipation stress may be caused by the subjects' frantic rush between games to select new weapons. Game anticipation stress did not seem to affect everyone, as could be seen by comparison with the previous subject.

Next, subject 8913's data from session 3 were mapped using his SOM generated with the data from session 6. In session 3, it seems that subject 8913 was greatly concerned about his character's death in the game (black). He was also very disturbed by the deaths of his comrades (red). He was not as concerned in session 3 about conflicts he had with the other players (yellow). As the sessions progress, 8913 seemed to be less concerned with his own character's death, yet continued to be concerned about the deaths of others on his team.

No elaborate plans were devised and executed by the team during session 3, rather, basic commands were issued. The subject exhibited a wide range of reactions to issuing commands. Only one cooperative event was noted by 8913 in session 3. It should also be noted that during session 3, subject 8913's character was alive for only 30:56 out of the 40:24 session game time. This allowed him less opportunity than the other subjects to come to the aid of others.

Finally, the data for subject 8913 from session 10 was processed through his SOM generated from session 6. The subject seemed to be greatly concerned about the death of others, although he was less disturbed about his own character's death than he was in session 3. He is still concerned with conflicts among the group. The yellow conflict point above represents two separate conflicts that occurred during the session. In addition, it also superimposes a red point representing the death of a comrade. Again, this outcome often happens with a SOM, since its mapping is not 1-1.

As to the remaining events of interest for 8913 during session 10, at this point in the study the subjects were conceiving and executing elaborate battle plans under the leadership of 8913 (and others, in cases where 8913's character was dead). These events are plotted in green. 8913 still had a wide range of reactions to issuing commands, likely due to each particular case. However, he did seem to be more comfortable with coming to the aid of others (light blue) than in session 6.

By the end of session 3, 8913 had emerged as the leader of the group. As time went on, he became more concerned about conflicts he had with other group members. He may have been reacting to concern about his position as leader. At times, 8913 exhibited stress at the beginning of games. As the battle plans he devised (along with other players) became more elaborate, he seemed to exhibit more stress upon their execution. He reacted very differently to executing commands, based on the situation. This continued to be the case throughout the study. As the sessions progressed, he seemed to be more comfortable with coming to the aid of others. From the beginning, he seemed to be very concerned about the deaths of other players and continued to be so throughout the study, even though he began to exhibit less stress about his own character's death. This would seem a trait that is exhibited by a leader.

Subject 6068's data from session 6 were used to train a SOM. That SOM was later used to chart his data from session 3 and session 10. It is important to note that subject 6068 was not present for sessions 7-9, and was reintroduced to the group at session 10. Therefore, one may expect him to exhibit a higher level of stress during session 10 than other subjects who were present for the entire study.

In session 6, there were two levels of high stress in the map (red background). More exploration is needed to determine what has caused this, but it may possibly be do to conflicting physiological parameters (i.e., one red area may be associated with high heart rate but no movement, and another area many be associated with movement and low heart rate).

The subject reacted more strongly to the beginning of a game than anything else. Game anticipation stress seemed to be a consistent trait with this particular subject. The subject also seemed to exhibit stress when he was assuming a following role (dark blue). But he seemed more comfortable with coming to the aid of others (light blue), as well as his own character's death (black). 6068 displayed some stress over the deaths of his comrades, but not to the extent that these events erupted to the high stress level.

Next, the data from session 3 was examined, using the same SOM. Again, he seemed to exhibit high stress at the start of new games. He also exhibited high stress at his character's death (black), or when he is assuming a following role (dark blue). It is interesting to note that like 8913, he seemed to be concerned over the deaths of comrades, although he did not exhibit the highest stress levels. There are two alternative reasons why this may be true. First of all, in this session, most of his comrades' deaths occurred at the end of games. In addition to exhibiting stress at the beginning of games, a jump in 6068's heart rate was observed at the end of games. Often, in this session, 6068 was observed to turn his head to look at another subject after his character had been killed in the game. This action may have led to a high stress mapping in the SOM. This hypothesis is supported by the following observation. When heart rate data was examined, it was discovered that for this session, the comrade deaths that occurred before the end of games were not accompanied by a spike in the heart rate of subject 6068.

Finally, the data from session 10 was displayed on the same SOM from session 6. It seemed that the subject exhibits stress in reaction to almost all events of interest in session 10. This plot seemed very similar to that of session 3. Recall that the subject was absent for sessions 7-9, and reintroduced in session 10. During his absence, his comrades had three sessions to train with a new game setting and map that he saw for the first time in session 10. He likely forgot some of the nuances of the game in the interim, as well. The result is that, although the subject seemed somewhat comfortable with the game during session 6, stress levels equivalent to the beginning of the session sequence were observed for this subject during session 10. Although 8086 exhibited more stress upon his reintroduction to the game, it seemed to have no effect on the other subjects' individual data (see 8913 above, and 7621 below).

The data examined for subject 6068 seem to indicate the following. He seemed to consistently exhibit the most stress at the beginning of a game. This was true even in session 6, when he had become accustomed to the game and became more comfortable with other events. Although he did not take a leadership role in the sessions, his data seem to indicate that he was not very comfortable in a follower role, either. His reintroduction into the game after a three session hiatus seemed to cause his stress levels to reset to their early session levels.

For subject 7621 it was decided to train his SOM using the data of session 4. His data from sessions 3 and 10 were tested through the trained network. It must be emphasized that a SOM is an unsupervised training method, and there is not a guarantee how the final map will look. In the case of subject 7621, the final map appears inverted from the previous subjects, with the red area of high stress located in the bottom right corner.

In addition, the convention of labeling commands as dark blue, and conflict as yellow was inverted. Given the location of the plotted command point, it was impossible to see it in blue as it was on a blue background. From the session 4 data, the subject does not seem to be very concerned about the deaths of others. If one looks at the points that are plotted, one might say 7621 does not seem to be very stressed about anything. If this were not the training data, one might be true. However, some events in the data necessarily map to the red (stress) area. A comparison of the video and physiological data did not yield any further insights about what may have been the stressful events for subject 7621 in session 4.

As to session 3, there were no elaborate plans executed in session 3. Thus, green was used to indicate a rare following statement from subject 7621. He expressed more stress at being in a following position (green) than he did at issuing a command (yellow). As noted previously in this report, later subject 7621 split off to a certain extent from subject 8913 to form his own team. In this session, the subject seems to be more concerned about lending aid to others (light blue) and the beginning of games (pink) then he does about his own character's death. The one death of a comrade experienced in the session is displayed in yellow as well, since it maps to the same point as when 7621 was issuing a command. In this case, the subject does not exhibit a great deal of stress.

Finally, the session 10 data for 7621 was mapped through the SOM. As there was more than one overlapping point, the data was split into two figures. The data seems to indicate that an interesting development occurred over the course of the study. By session 10, 7621 seems to be very concerned over the deaths of his comrades. An examination of 7621's heart rate data from session 10 supports this supposition. In fact, this comrade death data is beginning to look more like the data 8913 produced over the entire sessions. What could this mean? Recall that 7621 and 8913 split off to be in charge of their own teams. Could this be the signature of a leader? Another possibility is that it could be the signature of a team operating more as a unit. That is, the players are showing more interest in the game, are comfortable with each other, and are concerned about what happens to their comrades. Yet another option is that as time goes on, group members may tend to adopt the reactions of the team leader.

This artifact was not displayed in the other two subjects who participated in session 10. However, one was new to the study, having only played in 3 previous sessions, and the other was returning to the game after a 3 session hiatus.

In session 10, subject 7621 exhibited the same reaction to giving commands (yellow) as was observed with subject 8913. In addition, 7621 exhibited great stress over conflicts (dark blue), and coming to the aid of others (light blue).

No firm conclusions can be drawn from the data presented here. It is very interesting to note that in session 10, the data from 7621 began to look very much like the data of the leader, 8913. Several possibilities were given for this artifact. However, it was impossible to determine given the scope of the current study, what the cause may be.

Subject 4564 was present for only a small part of the experiment, and so his data was examined in detail for one session only. Session 7, the first session in which he participated, was used. The results are presented below.

No conflicts were observed between 4564 and other subjects during session 7. At first glance, the subject seems to react strongly at the beginning of most games (pink). However, a closer examination of the data revealed that the strongest responses were noted at the start of the first two games, after which, the subject's stressful responses to the anticipation of the game subsided. Recall that this was the first session in which this subject participated. The pattern can be attributed to him exhibiting uncertainty of the game in the beginning, then becoming more accustomed to it as the session wore on. Although this was the subject's first session, he seemed to exhibit at least moderate concern over the death of his comrades. This is similar to what was observed for subject 8913 during session 3. Of special note here is 4564's response to issuing commands (yellow). Although this was his first session, and he was breaking in to a clearly established hierarchy, he seems to be quite comfortable with issuing commands. In general, he seems more stressed by taking the following role (green), than by taking the leadership role. This is remarkable, considering the subject was a complete novice at the game and was routinely making inquiries concerning keyboard commands, etc.

No general conclusions on individual or group dynamics and physiology are made here. However, based on the data collected and processed for the five test subjects who participated in the study, the following observations were noted:

1) Subject 4859 seemed to be comfortable in the role of follower.

2) Subject 8913 (the leader of the group) seemed to exhibit more stress regarding conflict and the execution of plans as the study developed and the plans became more elaborate. Whether this was an expression of concern in retaining his position as leader is undetermined and remains a question for future study.

3) Subject 8913, from the earliest sessions, reacted with concern over the deaths of his comrades, even after his own character was dead. Whether or not this is the characteristic of a leader is an interesting question.

4) Subject 6068 seemed to consistently exhibit the most stress at the beginning of each game. In session 6, he seemed more relaxed in general and less affected by the events of the game than in session 3. He was absent for sessions 7-9, and upon his return in session 10, he displayed nearly the same stress responses as in session 3. His hiatus from the game apparently caused his stress responses to, in effect, reset.

5) By session 10, subject 7621's data began to look very much like subject 8913's. Midway through the study, although 8913 retained ultimate leadership, 7621 split off to be in charge of his own team. The fact that his data by session 10 began to resemble that of the leader's (showing high concern for comrades, etc.) lends support to the idea that such responses may be traits of a leader. Alternatively, it could also be the case that over time team members will begin to emulate the responses of the leader. Another possibility is that it is a signature of a team in cooperation.

6) Subject 4564, although he was not introduced to the game until session 7 and was a complete novice, seemed very comfortable in roles that required him to demonstrate leadership. An interesting hypothetical question is: would the group dynamics have evolved differently had 4564 been present for all sessions?

The preceding was a structured observation involving a very small group of subjects. What potential does it demonstrate for the MENTOR/PAL concept? The vision is for the final system to have feedback capability, and for the PAL to be a wireless device. It is possible to outfit every subject with a SOM or similar network on his/her PAL. Due to the fact that the computational cost of a SOM is carried in its training, checking new data points for their meaning on the map is quite cheap in terms of complexity. As such, it would be straightforward to program the PALs to monitor the general well being of their users. Action could be taken by MENTOR if the data were outside normal ranges.

Here is one possible scenario. The MENTOR/PAL© lab equipment has the capability to install eye tracking devices. Suppose two subjects were not looking at the computer screen, and their stress levels were rising. It is reasonable to assume they were involved in a conflict. If their stress levels approach high levels, it is likely the conflict is no longer constructive. Under such a situation, the PALs could issue a signal to MENTOR, and MENTOR could respond by instructing one of the other subjects to say, "Hey, we could use some help over here." Or MENTOR could instruct the two subjects having the conflict to "Look at the computer screen."

Studying the data from each individual is only half the story, the health of the team is important as well. How are they performing? Are they effective in their current configuration? What has worked in the past that can improve the situation today? In this work, a group trained self-organizing map was used as a first step to search for the answers to these questions.

The data vectors to the SOM were exactly the same as in the previous section. The only difference is that the data from all subjects were combined. Thus, the SOM would train based on the experiences of four subjects, not one. The data selected for training the group SOM was from session 3.

Figure 6:
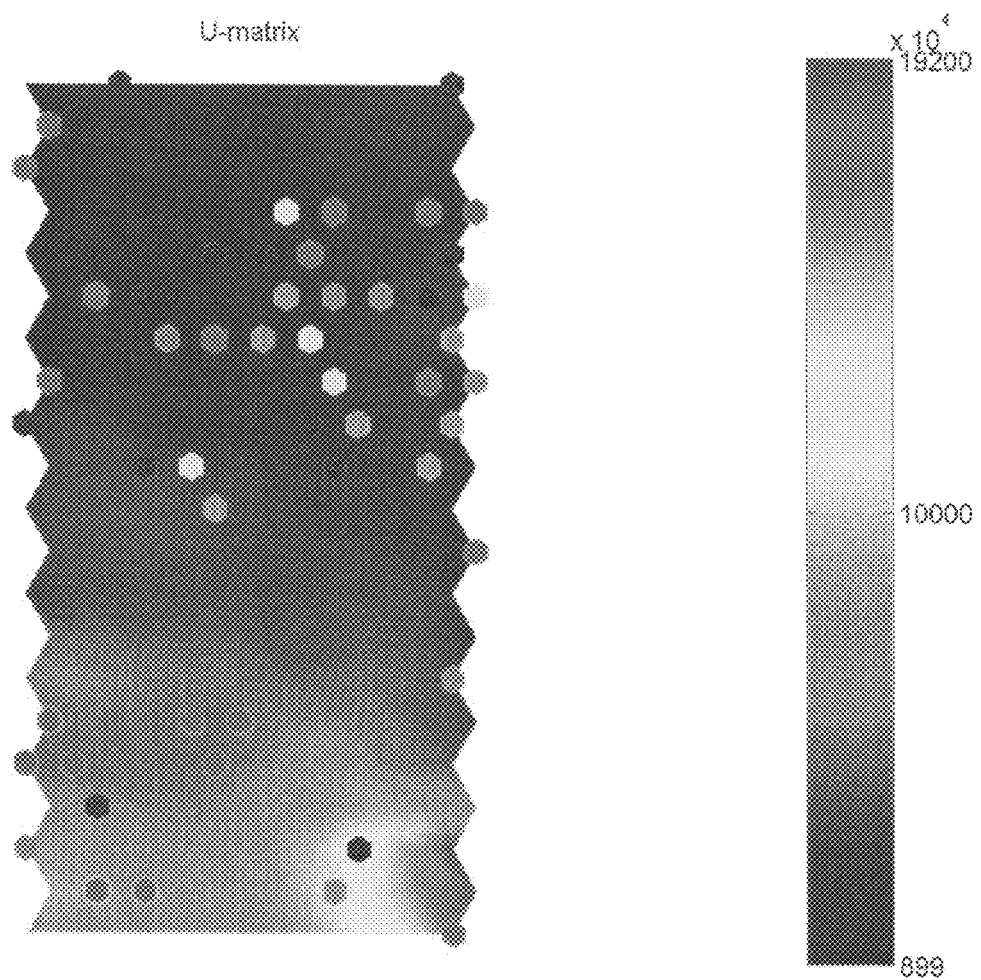
FIG. 6 is a U-matrix for the group's SOM generated according to the invention for one experimental session and showing events of interest from another experimental session.

In FIG. 6 is plotted the group SOM data for session 3. The data used for training was also for session 3. The data plotted in this figure is a conglomeration of all the session 3 data plotted individually in the previous session.

Figure 7:
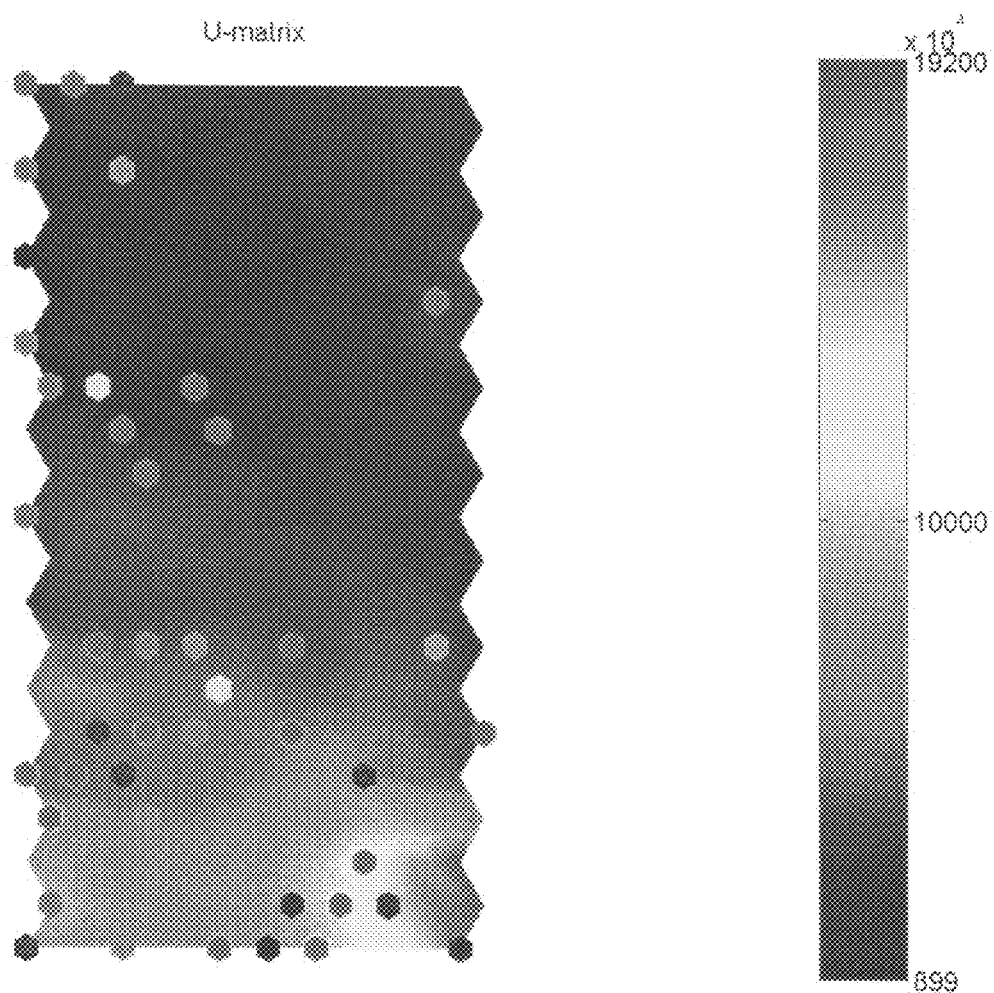
FIG. 7 is a U-matrix for the group's SOM generated according to the invention for one experimental session and showing events of interest from yet another experimental session.

In FIG. 7 is plotted group data from session 6, using the SOM generated with session 3 data. The points plotted are a combination of all individual points of interest for session 6. What is important to note is the comparison of session 6 with session 3. In general, in session 6 there are more points clustered in the region of the figure corresponding to less stress (blue background). Note the comparison of cooperation events (light blue). Comparing sessions 3 and session 6 one will note that in session 6 the subjects seem to be much more comfortable with coming to the aid of others. This could indicate a characteristic of desirable group behavior.

Unfortunately for this phase of the study, the group changed after session 6 and the same four subjects were never together again. Thus, results can be discussed from session 10, but only the data from the 3 subjects who were in session 6 can be included. To involve the data of subject 4563 on a SOM for which it was not trained would have no expectation of reliability.

The preceding exercise yielded a number of observations and posed a number of questions. It demonstrated that it may be possible to monitor the collective group "health" using a communally trained SOM. It also suggested that as a group becomes accustomed to working together, their data on the group map tends to migrate away from the high stress region. In addition, it implied that the introduction or reintroduction of a new member of the group affects the group health. Although the change may not be witnessed on the individual SOMs, it may be possible to observe the change on the group SOM. Further research is required in this area.

What does this imply for MENTOR? The results above seem to indicate that the individual SOM is not the complete story. There is much information about the group health and effectiveness that is potentially contained in the group SOM, and may not be present in the individual SOM. MENTOR could keep track of the group dynamics and effectiveness. For instance, in this application, the desirable would be to have a majority points in the "blue" area. If MENTOR began to see the group position drift away from the desirable area, it could consult with the PALs and potentially take action. A possible action may be to have a player sit out a game, or it may be to direct all the subjects to take a few moments to decide on a game strategy.

In phase one of this study, a MENTOR/PAL testbed was constructed, and found to be fully functional. In phase two, test subjects were recruited and asked to collaborate in a group video game. While the subjects played the game, the testbed equipment was used to collect various physiological and somatic data from the subjects. In addition, audio, video and game scores were recorded. A total of 10 sessions were conducted. In each session, the settings of the video game were adjusted to make the game more challenging. As an added stress, subjects were rotated in and out of the study, which forced the remaining subjects to become accustomed to a different group make up.

Analysis began by watching the subjects play the game and making observations concerning leadership and cooperation characteristics of the group. Game performance, both group and individual, was analyzed. Each session videotape was analyzed for examples of events of interest, including cooperation, conflict, leadership, and character death. These events of interest were time synchronized and compared to the heart rate data, using time/frequency techniques, to check for correlations. Correlations were found, and evidence of group cooperation was also isolated using the heart rate data.

The results of the heart rate analysis lead to the development of two different ways to approach the physiological and somatic data using self-organizing maps (SOMs). Both approaches were tested on actual subject data and found to yield interesting potential for future use. One approach was developed using separate SOMs to monitor the productivity of each individual. It was shown that a separate SOM was needed for each individual. The second approach used a conglomeration of data for the group to train a SOM to monitor the effectiveness of the group. It was shown that this SOM may be able to identify signatures of group cooperation and conflict. It was suggested that both types of SOMs be used in conjunction to improve the functionality of the group. Suggestions were given concerning how the two SOMs may be used together.

The following observations are particular to this study and are not meant to imply any conclusions outside of the study. However, they may suggest areas of future exploration using a larger subject set.

1) By the end of session 3, one subject emerged as the leader of the group. His physiological data demonstrated that he would react to concern over the mishaps of other test subjects, even after his character had been eliminated from the game.

2) By the end of session 6, a split occurred in the group, with an heir apparent branching off to be in charge of his own team. By the end of the study, his SOM data began to emulate that of the leader.

3) As the session progressed, the general trend observed in the SOM data through session 6 is that the subjects became more comfortable working together.

4) Individual SOM data suggests that some subjects seem comfortable in the role of follower.

5) Pulling a subject out of the game midway through the sessions, and reintroducing him for the last session, caused the subject's stress levels to reset to those encountered at the beginning of the sessions. It may also have an effect on the group. Although the effect on the group might not be observable in their individual SOMs, the group SOM of MENTOR seems to suggest the group was no longer as effective.

6) There was an indirect relationship in the game scores between killing effectiveness and time spent alive.

This report has only begun to explore the potential of a MENTOR/PAL system. Eventually, such systems could transform the way humans and computers work together, making humans a part of the system. Throughout the body of this report, suggestions were made for future study. They are included here.

1) Inclusion of EEG collection in future work may provide evidence of a correlation in what is termed in this report "low confidence events." The addition of EEG data would no doubt create a more accurate SOM.

2) Eye tracking technology could be implemented and incorporated into the SOM to make much of the classification of "high confidence events" automatic.

3) Running parallel studies using multiple subject groups on the same tasks would help to confirm or disprove the observations noted in this study.

4) The leader of the group seemed to exhibit stress at the death of others, and later, another member of the group seemed to behave the same way. Further testing should be done to determine if this is a signature of leadership, collaboration, or coincidence.

5) Further analysis should be performed on the effect on the group of having subjects enter and exit the study at prescribed intervals.

6) The MENTOR/PAL concept should be explored further to find if there is truly is a difference between individual and group physiological dynamics as was observed in this study.

7) More recorded data parameters could be included in the SOM training to likely produce a more complete picture of group effectiveness.

8) A specialized wavelet based transform could be designed to examine heart rate and other data with desired time/frequency resolution in spectral areas of interest.

The preceding example can be repeated with similar success by substituting the generically or specifically described reactants and/or operating conditions of this invention for those used in the preceding example.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of monitoring and intervening in, in real time, a collaboration between a plurality of subjects, the method comprising the steps of:
    measuring one or more indications of physiological and cognitive states of each of the plurality of subjects;
    communicating one or more of the indications to a monitoring computer system;
    with the monitoring computer system, comparing the indications with one or more models of previous collaborative performance of one or more of the plurality of subjects, wherein one or more of the models in the comparing step comprises a self-organizing map of multiple subjects of the plurality of subjects; and
    with the monitoring computer system, employing the results of the comparison to communicate commands or suggestions to one or more of the plurality of subjects.

2. The method of claim 1 wherein the measuring step comprises measuring using one or more of the group consisting of: electroencephalography devices; electro-oculography devices; electrocardiography devices; respiration rate devices; galvanic skin response devices; blood pulse volume devices; electromechanical motion sensors; and accelerometry devices.

3. The method of claim 1 wherein the comparing step comprises applying over time a sliding window Fourier transform to one or more of the indications.

4. The method of claim 1 wherein the self-organizing map is a self-organizing map of a single subject of the plurality of subjects.

5. The method of claim 1 wherein the self-organizing map is a self-organizing map of all of the plurality of subjects.

6. The method of claim 1 wherein the employing step comprises automatically communicating commands or suggestions.

7. The method of claim 1 wherein the employing step comprises displaying one or more of the indications or one or more results of the comparison to a monitoring human who initiates commands or suggestions.

8. The method of claim 7 wherein the communicating step comprises communicating visual images of one or more of the plurality of subjects and the method additionally comprises the step of displaying the visual images to the monitoring human.

9. An apparatus for monitoring and intervening in, in real time, a collaboration between a plurality of subjects, said apparatus comprising:
    means for measuring one or more indications of physiological and cognitive states of each of the plurality of subjects;
    means for communicating one or more of the indications to a monitoring computer system;
    a monitoring computer system that compares the indications with one or more models of previous collaborative performance of one or more of the plurality of subjects and employs the results of the comparison to communicate commands or suggestions to one or more of the plurality of subjects, wherein one or more of the models comprises a self-organizing map of multiple subjects of the plurality of subjects.

10. The apparatus of claim 9 wherein said means for measuring comprises one or more of the group consisting of: electroencephalography devices; electro-oculography devices; electrocardiography devices; respiration rate devices; galvanic skin response devices; blood pulse volume devices; electromechanical motion sensors; and accelerometry devices.

11. The apparatus of claim 9 wherein said monitoring computer system compares by applying over time a sliding window Fourier transform to one or more of the indications.

12. The apparatus of claim 9 wherein the self-organizing map is a self-organizing map of a single subject of the plurality of subjects.

13. The apparatus of claim 9 wherein said monitoring computer system automatically communicates commands or suggestions.

14. The apparatus of claim 9 wherein said monitoring computer system displays one or more of the indications or one or more results of the comparison to a monitoring human.

15. The apparatus of claim 14 wherein said means for communicating communicates visual images of one or more of the plurality of subjects and the apparatus additionally comprises one or more displays for displaying the visual images to the monitoring human.

16. A method of monitoring and intervening in, in real time, a collaboration between a plurality of subjects, the method comprising the steps of:

measuring one or more indications of physiological and cognitive states of each of the plurality of subjects;

communicating one or more of the indications to a monitoring computer system;

with the monitoring computer system, comparing the indications with one or more models of previous collaborative performance of one or more of the plurality of subjects; and with the monitoring computer system, employing the results of the comparison to communicate commands or suggestions to one or more of the plurality of subjects, by displaying one or more of the indications or one or more results of the comparison to a monitoring human who initiates commands or suggestions.

17. The method of claim 16 wherein the comparing step comprises applying over time a sliding window Fourier transform to one or more of the indications.

18. The method of claim 16 wherein the communicating step comprises communicating visual images of one or more of the plurality of subjects and the method additionally comprises the step of displaying the visual images to the monitoring human.

19. An apparatus for monitoring and intervening in, in real time, a collaboration between a plurality of subjects, said apparatus comprising:

means for measuring one or more indications of physiological and cognitive states of each of the plurality of subjects;

means for communicating one or more of the indications to a monitoring computer system, wherein said means for communicating communicates visual images of one or more of the plurality of subjects and the apparatus additionally comprises one or more displays for displaying the visual images to a monitoring human;

a monitoring computer system which displays one or more of the indications or one or more results of the comparison to the monitoring human and which monitoring computer system compares the indications with one or more models of previous collaborative performance of one or more of the plurality of subjects and employs the results of the comparison to communicate commands or suggestions to one or more of the plurality of subjects.

20. The apparatus of claim 19 wherein the self-organizing map is a self-organizing map of a single subject of the plurality of subjects.

* * * * *